United States Patent [19]

Leuenberger

[11] Patent Number: 5,668,183
[45] Date of Patent: Sep. 16, 1997

[54] WATER DISPERSIBLE COMPOSITIONS

[75] Inventor: Bruno Leuenberger, Basel, Switzerland

[73] Assignee: Roche Vitamins Inc., Paramus, N.J.

[21] Appl. No.: 694,141

[22] Filed: Aug. 8, 1996

Related U.S. Application Data

[63] Continuation of Ser. No. 430,663, Apr. 28, 1995, abandoned, which is a continuation of Ser. No. 41,255, Apr. 1, 1993, abandoned.

[30] Foreign Application Priority Data

Apr. 14, 1992 [CH] Switzerland ............... 1238/92
Jan. 22, 1993 [CH] Switzerland ............... 186/93

[51] Int. Cl.⁶ .............. A61K 31/07; A61K 31/70; A61K 31/595; A61K 31/355
[52] U.S. Cl. .............. 514/725; 514/22; 514/168; 514/458; 514/560; 514/777; 514/904; 514/942
[58] Field of Search .............. 514/22, 168, 458, 514/725, 904, 777, 942, 560

[56] References Cited

U.S. PATENT DOCUMENTS

| | | | |
|---|---|---|---|
| 2,680,113 | 6/1954 | Adler et al. | 530/500 |
| 2,905,558 | 9/1959 | Adams | 514/22 |
| 3,085,939 | 4/1963 | Wruble et al. | 514/938 |
| 3,384,545 | 5/1968 | Aiello et al. | 514/936 |
| 3,726,850 | 4/1973 | Detroit | 514/22 |
| 3,733,405 | 5/1973 | Derrig | 514/731 |
| 3,776,857 | 12/1973 | Lindner | 514/731 |
| 3,934,017 | 1/1976 | Gallay et al. | 514/367 |
| 4,228,159 | 10/1980 | MacMillan | |
| 4,405,552 | 9/1983 | Miesel | 514/353 |
| 4,666,522 | 5/1987 | Hollis et al. | |
| 4,810,726 | 3/1989 | Bistrian et al. | 514/398 |
| 4,988,799 | 1/1991 | Samson et al. | 514/22 |

FOREIGN PATENT DOCUMENTS

| | | |
|---|---|---|
| 36573/89 | 6/1989 | Australia . |
| 347 751 | 6/1989 | European Pat. Off. . |
| 1 517 044 | 5/1963 | Germany . |
| 3240862 | 5/1984 | Germany . |
| 3410348 | 10/1985 | Germany . |
| 3 837 957 | 11/1988 | Germany . |
| 674739 | 2/1979 | U.S.S.R. . |
| 91/11110 | 1/1991 | WIPO . |

*Primary Examiner*—Raymond Henley, III
*Attorney, Agent, or Firm*—George W. Johnston; Patricia S. Rocha-Tramaloni; Raina Semionow

[57] ABSTRACT

Novel, stable, cold water-dispersible preparations of fat-soluble substances contain a water-soluble or water-dispersible lignin derivative as the matrix component. These preparations are manufactured by preparing an aqueous emulsion of the fat-soluble substance(s) and the water-soluble or water-dispersible lignin derivative and, if desired, converting this emulsion into a dry powder. The preparations in accordance with the invention can be used not only for animal nutrition but also for human nutrition.

4 Claims, No Drawings

WATER DISPERSIBLE COMPOSITIONS

This is a continuation, of application Ser. No. 08/430,663 filed Apr. 28, 1995, now abandoned, which is a continuation of application Ser. No. 08/041,255, filed Apr. 1, 1993, now abandoned.

BACKGROUND OF THE INVENTION

The present invention is concerned with novel, stable, cold water-dispersible preparations of fat-soluble substances and with a process for their manufacture.

Cold water-dispersible preparations of fat-soluble substances, e.g. the fat-soluble vitamins, carotenoids, polyunsaturated fatty acids and the like, play an important rôle in the field of human and animal nutrition. Such preparations are usually marketed in the form of emulsions or dry powders because of their water-insolubility or also their more or less pronounced stability and ease of handling. It is a common feature of such preparations that the active substances, i.e. the fat-soluble substances, are usually enveloped with a matrix component (protective colloid), e.g. gum arabic or gelatine. This matrix component is responsible, inter alia, for the protection of the active substance or for its stabilization, for an optimum resorption and for the water-dispersibility of the final preparation which may be required. As the matrix component (protective colloid) there is normally used gelatine which originates from warm-blooded animals and which accordingly also has certain disadvantages. Merely by way of example there are to be mentioned here the fact that preparations based on such gelatine cannot be used worldwide for religious reasons, that without an expensive production process this gelatine and accordingly also the pulverous preparations manufactured therewith do not always have the desired dispersibility in cold water, etc.

SUMMARY OF THE INVENTION

In accordance with the invention it has now been found that all of these disadvantages can be eliminated when a water-soluble or water-dispersible lignin derivative is used in place of gelatine from warm-blooded animals.

DETAILED DESCRIPTION

The stable, cold water-dispersible preparations of fat-soluble substances provided by the invention accordingly contain a water-soluble or water-dispersible lignin derivative as the matrix component.

The term "cold water-dispersible preparations" signifies in the scope of the present invention not only liquid but also corresponding solid application forms. The solid application forms, i.e. preparations which are present in pulverous form, are preferred. The term "fat-soluble substances" embraces in the scope of the present invention especially the fat-soluble vitamins A, D, E and K, carotenoids such as, for example, β-carotene, astaxanthin, apocarotenal, canthaxanthin, apoester, citranaxanthin and zeaxanthin, as well as multiply-unsaturated (polyunsaturated) fatty acids. However, there readily come into consideration other fat-soluble substances which play a rôle in human or animal nutrition. These substances, such as the previously mentioned, are usually marketed in the form of emulsions or dry powders because of their insolubility in water or also their more or less pronounced stability and ease of handling. Here there can be mentioned, in particular, oils and fats such as, for example, sunflower oil, palm oil and beef fat.

The lignin derivatives present in the preparations in accordance with the invention are especially industrially produced products which contain ligninsulphonates having the widest variety of cations. Sodium, calcium and ammonium liginsulphonate are however of particular interest. A preparation in accordance with the invention can contain a single lignin derivative or a mixture of several lignin derivatives as the lignin derivative. Furthermore, the lignin derivative present in the preparations in accordance with the invention can be part of an industrially produced product which contains further components in addition to the lignin derivatives.

As is known, the biopolymer lignin is one of the main components of wood and occurs together with cellulose in plants, especially in wood. Wood, depending on the type, contains about 16 to 37% lignin. Considered chemically, lignin consists of irregular polymers of methoxylated phenylpropane monomers (p-coumaryl alcohol, coniferyl alcohol, sinapyl alcohol etc.) having a molecular weight estimated to be at least 20 kD. In a first step in the production of cellulose the wood is decomposed, which is effected in most cases by treatment with sulphite lyes at 125°–180° C. Thereby, the cellulose is liberated and the lignin is converted into a water-soluble derivative, ligninsulphonate (also known as sulphite lignin). On a smaller scale, the decomposition of wood is also effected by treating the wood with sodium hydroxide and disodium tetrasulphide (the "Kraft process"). The lignin obtained in this process is referred to as Kraft lignin or sulphate lignin and is not water-soluble at neutral pH. More recent processes for the production of cellulose use organic solvents, e.g. alcohol, also mixed with water, for the decomposition of wood, and the thus-produced lignin is referred to as organosolv lignin. This form of lignin is likewise not water-soluble. At present, primarily ligninsulphonates and Kraft lignins are commercially available. Frequently, after the decomposition of the wood, the cellulose is separated and the resulting ligninsulphonate-containing solution is concentrated to about 50% solid content and sold in this form. Most producers also offer pulverous products which have been obtained by spray-drying the solutions, and these solid forms also contain various saccharides in considerable amounts in addition to lignin. Some producers manufacture lignin derivatives having a relatively high content of ligninsulphonate(s) from the primary (crude) lignin-sulphonates by enzymatic removal of the saccharides and, if necessary, by purification, for example by ultracentrifugation. The Kraft lignins, which are also offered, can be sulphonated in order to achieve water-solubility and the sulphonation products are suitable as lignin derivatives for use in the preparations in accordance with the invention. Commercial ligninsulphonate products typically consist of about 40–90% ligninsulphonate and smaller amount of various saccharides, ash, carbohydrates, acetates, formates, resins etc., with the composition depending very much on the quality of the wood which is used. Such water-soluble ligninsulphonate products are also suitable for use in the preparations in accordance with the invention. In general, not only the crude products having a relatively high content of saccharides and additional byproducts but also the aforementioned purified lignin derivatives can be used in the preparations in accordance with the invention, provided that such lignin derivatives are water-soluble or at least water-dispersible. Examples of well-suited lignin derivatives are:

Orzan ®S (sodium ligninsulphonate from ITT Rayonier, Stamford, CT, and Seattle, WA, USA);
Orzan ®A (ammonium ligninsulphonate from ITT Rayonier);
Attisol ®10  } (calcium and, repsectively, sodium ligninsulphonate
Attisol ®20  } from Cellulose Attisholz AG, Switzerland).

The above four products are primary ligninsulphonate products having a relatively high sugar content.

Orzan®LS (sodium ligninsulphonate having an enzymatieally reduced sugar content; ITT Rayonier);

Orzan®CD (sodium ligninsulphonate having a sugar content which is further reduced; ITT Rayonier);

Temsperse® S-001 (sodium ligninsulphonate having a low sugar content; from Temfibre Inc., Temiscaming, QC, Canada);

Tembind® A-001 (sugar-containing ammonium ligninsulphonate from Temfibre Inc.);

Reax® 910 [(sodium-) sulphonated Kraft lignin from Westvaco Chemicals, Charleston Heights, S.C., USA];

Polyfon® O [(sodium-) sulphonated Kraft lignin from Westvaco Chemicals; this product must be brought to about pH 5.5, e.g. with hydrochloric acid, prior to use];

as well as Wafolin® (sugar-containing calcium ligninsulphonate from Holmen LignoTech GmbH, Karlsruhe, Germany).

Further, the preparations in accordance with the invention can also have an additional matrix component, e.g. a protective colloid, in addition to the water-soluble or water-dispersible lignin derivative. Gelatine (gelatine from warm-blooded animals and/or fish gelatine) is especially suitable for this purpose, because no compatibility problems occur. Moreover, the lignin derivative can be used in combination with a carrier such as, for example, maltodextrin or an (additional) sugar.

The weight ratio of the fat-soluble substances to the accompanying substances (lignin derivative(s), water, sugar etc.) present in the finished product (essentially dry powder) is generally about 1:100 to about 80:100, with the precise ratios depending on the particular biological requirements of the active substances (fat-soluble substances) and on the demands for homogeneous and sufficiently fine distribution of the finished preparations in the application forms provided for consumption. Should further stabilizing substances be required or desired in the preparations, then these can usually be incorporated during the manufacturing process.

The preparations in accordance with the invention can be manufactured, in principle, by preparing an aqueous emulsion of the fat-soluble substance(s) and the water-soluble or water-dispersible lignin derivative and, if desired, converting this emulsion into a dry powder. This manufacturing process represents a further object of the present invention, as do emulsions which have been diluted further with water if desired.

Generally, all components, i.e., inter alia, the lignin derivative, excluding the fat-soluble substance(s), are first dissolved in water, which is conveniently accelerated by vigorous stirring. Moreover, it has been found to be advantageous to carry out this process step at elevated temperature, especially in the temperature range of 20° C. to 90° C. The so-called matrix is obtained in this manner. Then, the fat-soluble substance or a mixture of several such substances is emulsified in this matrix, also advantageously with vigorous stirring or by means of ultrasonics or similar technology. The pressure and the temperature in this procedure do not represent critical parameters, and the procedure can be carried out readily at temperatures of about room temperature to about 70° C. and at atmospheric pressure. In the manufacture of the emulsion there can, of course, be used conventional adjuvants which are normally used in such preparations, such as, for example, sugars, e.g. saccharose; sugar alcohols; starch derivatives, e.g. maltodextrin; milk proteins, e.g. sodium caseinate; or also vegetable proteins, e.g. soya protein, potato protein and wheat protein. Should further stabilizing substances be required or desired in the thus-manufactured preparations, then these can normally be dissolved in the oil phase, i.e. in an incorporated liquid fat-soluble substance. Further, emulsifiers such as, for example, ascorbyl palmitate and sugar esters can be used in the manufacture of the emulsion.

The conversion of a thus-manufactured emulsion, which depending on the ingredients generally contains from about 40 to about 60 weight percent of fat-soluble substance(s), into a dry powder can be effected e.g. by normal spray-drying, the double dispersion process or also the starch-catch process. In the latter process, the sprayed emulsion droplets are collected in a bed of starch and the drying is carried out subsequently. Where desired, the emulsion to be sprayed can be diluted with water. In such cases the emulsion can contain for practical purposes as little as about 1 weight percent of fat-soluble substance(s).

The present invention is also concerned with the use of a water-soluble or water-dispersible lignin derivative as a matrix component for the manufacture of stable, cold water-dispersible preparations of fat-soluble substances.

The manufacture of the preparations in accordance with the invention is generally simpler than that of conventional preparations using other matrix components, e.g. gelatine. This is because of the good water-solubility of the lignin derivatives used in accordance with the invention and their outstanding emulsifiability. The good water-solubility permits a significant lowering of the water content of the emulsion, which leads to savings in the manufacturing costs and/or to an increase in manufacturing capacity. The good emulsifiability together with the relatively low water content of the emulsion and the resulting relatively high viscosity lead to a very fine internal phase of the emulsion with an extremely narrow particle size distribution, which brings about a very good stability of the emulsion and an improved bioavailability of the fat-soluble substances present therein. Further, the preparations in accordance with the invention have a relatively small amount of the respective fat-soluble substance on the surface of the particles, which indicates the quality of the imbedding of the fat-soluble substance in the matrix, i.e. the good enveloping capacity of the lignin derivative which is used.

In general, the preparations in accordance with the invention have a good cold water-dispersibility and—when they are in dry form (as a solid, pulverous application form)—a good flowability. Further, it has been found that the preparations have a relatively low hygroscopicity.

The preparations in accordance with the invention can be used not only for animal nutrition but also for human nutrition. In certain instances it can also be convenient not to convert the manufactured emulsions into dry powders, but to use them directly. The preparations in accordance with the invention are preferably suitable for the formulation of fat-soluble substances in the field of animal nutrition.

The present invention is illustrated by the following Examples.

EXAMPLE 1

197.4 g of Orzan®S (sodium ligninsulphonate from ITT Rayonier, Stamford, Conn. and Seattle, Wash., USA) are dissolved in 99 g of water at 50° C. in a reaction vessel using a stirrer equipped with a dissolution disk, the stirring velocity being 2000 rpm. 222.6 g of dl-$\alpha$-tocopherol acetate (Roche), warmed to 70° C., are added to the resulting solution within 5 minutes at a stirring velocity of 5000 rpm. The resulting emulsion is emulsified (5000 rpm) at 50° C. for a further 30 minutes. This emulsion has a particle size of the internal phase (tocopherol acetate) of 193±49 nm (laser diffraction: PCS spectrometer Coulter N4S, France). The emulsion is diluted with 692 g of water and spray-dried (air temperature: inlet 220° C., outlet 72° C.) using a spray drier (Minor from the company Niro Atomizer, Denmark). In this manner there are obtained about 300 g of powder, the flowability of which is improved by intermixing 1% silicic acid Sipernat®50S. The product has a tocopherol acetate content of 53.9%. 7.3% of the total tocopherol acetate is situated on the surface of the powder particles and can be washed off therefrom with cyclohexane. The spray-dried powder has good flow properties and exhibits an excellent dispersibility in cold water.

EXAMPLE 2

An emulsion is manufactured analogously to the procedure described in Example 1 using 197.4 g of Attisol®10 (calcium ligninsulphonate from Cellulose Attisholz AG, Switzerland), 222.6 g of dl-α-tocopherol acetate and 110 g of water. The particle size of the internal phase here is 203 nm. The emulsion is diluted with 730 g of water and spray-dried. The pulverous product contains 49.0% of tocopherol acetate, of which 4.9% can be washed off with cyclohexane.

EXAMPLE 3

An emulsion, which has a particle size of the internal phase of 211±50 nm, is manufactured analogously to the procedure described in Example 1 using 197.4 g of Orzan®CD (sodium ligninsulphonate, ITT Rayonier), 222.6 g of dl-α-tocopherol acetate and 160 g of water. After dilution with 655 g of water the emulsion is spray-dried. The spray-dried powder has a content of 52.0% of tocopherol acetate, of which 69% can be washed off with cyclohexane.

The amount of tocopherol acetate which can be washed off is considerably higher in this product than is the case in Example 1. This shows that different ligninsulphonate qualities give different products.

EXAMPLE 4

Analogously to the procedure described in Example 1, 127.1 g of Orzan®LS (sodium ligninsulphonate, ITT Rayonier), 31.2 g of 45% aqueous solution of fish gelatine (Norland Products Inc., New Brunswick, N.J., USA), 159 g Of dl-α-tocopherol acetate and 100 g of water are processed to an emulsion, the internal phase of which has a particle size of 467±160 nm. After the addition of 502 g of water the emulsion is spray-dried. The product obtained has a content of 53.6% of tocopherol acetate, of which 33% can be washed off with cyclohexane.

EXAMPLE 5

46.8 g of Orzan®S (sodium ligninsulphonate, ITT Rayonier), 141.2 g of maltodextrin MD05 (Roquette, France), 212 g of dl-α-tocopherol acetate and 94 g of water are processed to an emulsion analogously to the procedure described in Example 1. The internal phase of this emulsion has a particle size of 337±86 nm. After the addition of 650 g of water the emulsion is spray-dried. The pulverous product contains 53.0% of to copherol acetate, of which 17.7% can be washed off with cyclohexane.

EXAMPLE 6

An emulsion in which the particle size of the internal phase is 277±85 nm is manufactured analogously to the procedure described in Example 1 using 113.4 g of Orzan®S (sodium ligninsulphonate, ITT Rayonier), 306.6 g of dl-α-tocopherol acetate and 57.0 g of water. The spray-drying of the emulsion is effected after dilution with 783 g of water. The spray-dried powder has a content of 74.3% of tocopherol acetate, of which 52% can be washed off with cyclohexane.

The amount of tocopherol acetate which can be washed off is substantially higher in this Example than in the case of Example 1 and is due to the higher tocopherol acetate content.

EXAMPLE 7

87.8 g of Orzan®S (sodium ligninsulphonate, ITT Rayonier) are dissolved in 60.0 g of water at 45° C. in a reaction vessel (11) using a stirrer equipped with a dissolution disk, the stirring velocity being 2000 rpm. 16.5 g of β-carotene (crystalline, Roche) and 3.3 g of ethoxyquin are dissolved in 230 ml of chloroform at 65° C. during 30 minutes in a 500 ml Erlenmeyer flask. This second solution is emulsified within 12 minutes in the warm first solution in the 1l reaction vessel while stirring at 5000 rpm. The resulting emulsion is diluted with an additional 50 g of water and emulsified at 5000 rpm for 30 minutes. The particle size of the internal phase (β-carotene in chloroform) of this emulsion is 173±42 nm. The chloroform is distilled off at 50° C. in a water-jet vacuum using a rotary evaporator. The particle size of the internal phase (β-carotene) of this emulsion is now 136±51 nm.

900 g of corn starch, fluidized by means of silicic acid and cooled to about 5° C., are placed in a laboratory spray tank. The emulsion is sprayed into this starch and the resulting particles, which are enveloped with starch, are sieved from the starch and dried at room temperature. The pulverous product has a content of β-carotene of 10.2% and exhibits good dispersibility in cold water. 0.1% of the β-carotene can be washed off from this product with methylene chloride. The colour intensity (absorption) in water of this product is 1100 (1% solution, 1 cm layer thickness).

EXAMPLE 8

An emulsion is manufactured analogously to the procedure described in Example 7 using 175.6 g of Attisol®10 (calcium ligninsulphonate, Cellulose Attisholz), 150 g of water, 32.5 g of canthaxanthin (crystalline, Roche), 3.0 g of ethoxyquin and 350 ml of chloroform. After the addition of a further 59 g of water and removal of the chloroform using a rotary evaporator the emulsion/suspension is converted into a powder by spraying into a laboratory spray tank. The powder contains 13.2% of canthaxanthin, of which 0.2% can be washed off with chloroform. The particle size of the internal phase (canthaxanthin) is 140±34 nm and the product has a colour intensity in water of 1272 (1% solution, 1 cm layer thickness).

EXAMPLE 9

An emulsion is manufactured analogously to the procedure described in Example 7 using 175.6 g of Orzan®S (sodium ligninsulphonate, ITT Rayonier), 180 g of water, 32 g of citranaxanthin (crystalline, Roche), 4.9 g of ethoxyquin and 510 ml of chloroform. After the addition of 40 ml of water the chloroform is removed on a rotary evaporator to give an emulsion. A solution of 32 g of citranaxanthin and 4.9 g of ethoxyquin in 510 ml of chloroform is emulsified into this emulsion. After again removing the chloroform on a rotary evaporator the emulsion is converted into a powder using a laboratory spray tank analogously to Example 7. The resulting powder contains 17.8% of citranaxanthin, of which 0.3% can be washed off with chloroform. The particle size of the internal phase (citranaxanthin) is 215±59 nm and the product has a colour intensity in water of 1172 (1% solution, 1 cm layer thickness).

EXAMPLE 10

An emulsion is manufactured analogously to the procedure described in Example 1 using 197.4 g of Orzan®A (ammonium ligninsulphonate, ITT Rayonier), 222.6 g of dl-a-tocopherol acetate and 99 g of water and is spray-dried after the addition of a further 692 g of water. The resulting powder contains 53% of dl-a-tocopherol acetate, of which 8% can be washed off with cyclohexane. The particle size of the internal phase (dl-a-tocopherol acetate) of the water-reconstituted emulsion is 198±52 nm.

EXAMPLE 11

An emulsion is manufactured analogously to the procedure described in Example 1 using a warm solution (45° C.) of 200 g of Attisol®10 (calcium ligninsulphonate, Cellulose Attisholz) in 90 g of water and a warm solution (60° C.) containing 82.5 g of vitamin A mixture Feed Grade Type B (Roche) and 3.6 g of ethoxyquin. After the addition of 196 g of water this emulsion is spray-dried. The resulting powder contains 501 122 IU/g of vitamin A, of which 0.03% can be washed off with cyclohexane. The internal phase (vitamin A) has a particle size of 126±34 nm.

EXAMPLE 12

An emulsion is manufactured analogously to the procedure described in Example 11 using 200 g of Attisol®10 (calcium ligninsulphonate, Cellulose Attisholz), 112 g of vitamin A mixture Feed Grade Type B (Roche) and 100 g of water. After the addition of 110 g of water this emulsion is sprayed into corn starch using a laboratory spray tank analogously to Example 7. The resulting product contains 585 655 IU/g of vitamin A, of which 0.1% can be washed off with cyclohexane. The particle size of the internal phase (vitamin A) is 156±42 nm.

EXAMPLE 13

An emulsion is manufactured analogously to the procedure described in Example 1 using a warm solution (45° C.) of 200 g of Orzan®S (sodium ligninsulphonate, ITT Rayonier) in 90 g of water and a warm solution (65° C.) of 6.18 g of vitamin $D_3$ (technical quality, Roche) and 3.09 g of ethoxyquin in 6.18 g of arachis oil. After the addition of a further 125 g of water the emulsion is spray-dried. The resulting powder has a vitamin $D_3$ content of 488 000 IU/g. The particle size of the internal phase (vitamin $D_3$ in arachis oil) is 96:1:24 nm.

EXAMPLE 14

An emulsion is manufactured analogously to the procedure described in Example 1 using 100 g of Reax®910 [(Na-) sulphonated Kraft lignin, Westvaco Chemicals, Charleston Heights, S.C., USA], 112.5 g of dl-a-tocopherol acetate and 105 g of water. After the addition of a further 298 g of water an emulsion having a particle size of the internal phase of 140±38 nm is obtained. The resulting emulsion can be left as an emulsion or can be spray-dried analogously to Example 1.

EXAMPLE 15

An emulsion is manufactured analogously to the procedure described in Example 1 using 100 g of Temsperse®S-001 (sodium ligninsulphonate, Temfibre Inc., Témiscaming, QC, Canada), 112.8 g of dl-a-tocopherol acetate and 80 g of water. After the addition of a further 323 g of water there is obtained an aqueous tocopherol acetate emulsion having a particle size of the internal phase of 183±55 nm.

I claim:

1. A dry pulverous composition prepared by drying an emulsion, comprising a fat soluble substance and a water dispersible lignin derivative in an amount effective to render said fat soluble substance dispersible in water, wherein said lignin derivative is a matrix component forming an enveloping film around the fat soluble substance and the fat soluble substance is selected from the group consisting of vitamins A, D, E and K; carotenoids; polyunsaturated fatty acids and mixtures thereof, wherein said emulsion has an internal particle size not larger than about 467 nm.

2. The composition of claim 1, wherein the fat soluble substance is β-carotene, astaxanthin, apocarotenal, canthaxanthin, apoester, citranaxathin, zeaxanthin or mixtures thereof.

3. The composition of claim 1 wherein the lignin derivative is sodium, calcium or ammonium liginsulphonate or mixtures thereof.

4. An emulsion having an internal particle size not larger than about 467 nm, comprising a fat soluble substance and a water dispersible lignin derivative in an amount effective to render said fat soluble substance dispersible in water, wherein said lignin derivative is a matrix component forming an enveloping film around the fat soluble substance and the fat soluble substance is selected from the group consisting of vitamins A, D, E and K; carotenoids; polyunsaturated fatty acids and mixtures thereof.

* * * * *